(12) United States Patent
Filler et al.

(10) Patent No.: US 6,919,067 B2
(45) Date of Patent: Jul. 19, 2005

(54) COMPOSITIONS COMPRISING A TISSUE GLUE AND THERAPEUTIC AGENTS

(75) Inventors: Aaron Gershon Filler, Los Angeles, CA (US); Andrew Michael Lindsay Lever, Cambridge (GB)

(73) Assignee: Syngenix Limited (GB)

( * ) Notice: Subject to any disclaimer, the term of this patent is extended or adjusted under 35 U.S.C. 154(b) by 195 days.

(21) Appl. No.: 10/015,162

(22) Filed: Dec. 11, 2001

(65) Prior Publication Data

US 2002/0168319 A1 Nov. 14, 2002

Related U.S. Application Data

(63) Continuation of application No. 08/776,737, filed as application No. PCT/GB95/01330 on Jun. 7, 1995, now abandoned, and a continuation-in-part of application No. 08/473,697, filed on Jun. 7, 1995, now Pat. No. 5,948,384, which is a continuation of application No. 07/988,919, filed as application No. PCT/EP91/01780.

(30) Foreign Application Priority Data

| Jul. 21, 1994 | (GB) | ............................................. 9414684 |
| Jul. 25, 1994 | (GB) | ............................................. 9415405 |
| Feb. 6, 1995 | (GB) | ............................................. 9502246 |
| Feb. 21, 1995 | (GB) | ............................................. 9503357 |

(51) Int. Cl.$^7$ ........................................... A61M 36/14
(52) U.S. Cl. .................... 424/1.29; 424/1.25; 424/1.11; 424/1.49; 424/1.33
(58) Field of Search .............................. 424/1.11, 1.25, 424/1.29, 1.33, 1.49

(56) References Cited

U.S. PATENT DOCUMENTS

| 4,430,320 A | 2/1984 | Shigematsu et al. |
| 4,452,773 A | 6/1984 | Molday |
| 4,479,940 A | 10/1984 | Bizzini |

(Continued)

FOREIGN PATENT DOCUMENTS

| EP | 0 455 093 A2 | 11/1991 |
| EP | 05/34178 A3 | 3/1993 |
| WO | WO 86/01112 A1 | 2/1986 |
| WO | WO 88/00060 A1 | 1/1988 |
| WO | WO 89/09625 A1 | 10/1989 |
| WO | WO 90/01295 A1 | 2/1990 |
| WO | WO 91/01144 A1 | 2/1991 |
| WO | WO 91/04014 A1 | 4/1991 |
| WO | WO 92/09301 A1 | 6/1992 |
| WO | WO 92/11846 A1 | 7/1992 |
| WO | WO 92/22312 A1 | 12/1992 |
| WO | WO 93/05067 A1 | 3/1993 |
| WO | WO 93/05815 A1 | 4/1993 |
| WO | WO 94/20133 A1 | 9/1994 |

OTHER PUBLICATIONS

Bhargava et al. "Labeling of Monoclonal antibodies with radionuclides," 1989, Seminars in Nuclear Medicine, vol. 19, pp. 187–201.*
Bhargava et al. "Labeling Monoclonal Antibodies with Radionuclides" *Seminars in Nuclear Medicine*, Jul. 1989, pp. 187–201, vol. 19, No. 3.
Database WPI, Week 9306, Derwent Publications Ltd., London, GB; AN 93–049554 (06).
World Patent Index, abstract of J P–A–500097, Jan. 8, 1993.
Gallagher, J.E. et al. "Sialic Acid Mediates the Initial Binding of Positively Charged Inorganic Oarticles to Alveolar Macrophage Membranes" *Am. Rev. Respir. Dis.*, 1987, pp. 1345–1352, vol. 135, No. 6 (abstract only).

(Continued)

*Primary Examiner*—Shengjun Wang
(74) *Attorney, Agent, or Firm*—Saliwanchik, Lloyd & Saliwanchik (57) ABSTRACT

The present invention concerns compositions comprising a radiotherapeutic agent, or an agent which can be converted to a radiotherapeutic, and a tissue glue. The compositions of the present invention are particularly useful for providing local radiotherapy. The present invention also concerns methods of using the compositions of the invention, particularly for radiotherapy.

22 Claims, 3 Drawing Sheets

U.S. PATENT DOCUMENTS

| | | |
|---|---|---|
| 4,552,145 A | 11/1985 | Riley et al. |
| 4,594,336 A | 6/1986 | Bizzini |
| 4,690,130 A | 9/1987 | Mirell |
| 4,752,567 A | 6/1988 | De Brabander et al. |
| 4,813,399 A | 3/1989 | Gordon |
| 4,827,945 A | 5/1989 | Groman et al. |
| 4,849,210 A | 7/1989 | Widder |
| 4,863,715 A | 9/1989 | Jacobsen et al. |
| 4,927,916 A | 5/1990 | Matsueda et al. |
| 5,019,369 A | 5/1991 | Presant et al. |
| 5,043,101 A | 8/1991 | Gordon |
| 5,077,035 A | 12/1991 | Wieland et al. |
| 5,169,933 A | 12/1992 | Anderson et al. |
| 5,226,877 A | 7/1993 | Epstein |
| 5,248,772 A | 9/1993 | Siiman et al. |
| 5,290,552 A | 3/1994 | Sierra et al. |
| 5,342,283 A * | 8/1994 | Good ............................ 600/8 |
| 5,382,468 A | 1/1995 | Chagnon et al. |
| 5,424,288 A | 6/1995 | Order |
| 5,492,814 A | 2/1996 | Weissleder |
| 5,554,498 A | 9/1996 | Filler et al. |
| 5,614,652 A | 3/1997 | Filler et al. |
| 5,631,011 A | 5/1997 | Wadstrom |

OTHER PUBLICATIONS

Menetrey, D. "Retrograde Tracing of Neural Pathways with a Protein–Gold Complex" *Histochemistry*, 1985, pp. 391–395, vol. 83, No. 5 (abstract only).

Haschke, Richard H. et al. "Preparation and Retrograde Axonal Transport of an Antiviral Drug/Horseradish Peroxidase Conjugate" *Journal of Neurochemistry*, 1980, pp. 1431–1435, vol. 35, No. 6.

* cited by examiner

COMPOSITIONS COMPRISING A TISSUE GLUE AND THERAPEUTIC AGENTS

CROSS-REFERENCE TO RELATED APPLICATIONS

This application is a continuation of U.S. application Ser. No. 08/776,737, filed May 5, 1997, now abandoned, which is a national stage application of International Application No. PCT/GB95/01330, filed Jun. 7, 1995, and a continuation-in-part of U.S. application Ser. No. 08/473,697, filed Jun. 7, 1995, now U.S. Pat. No. 5,948,384, which is a continuation of U.S. application Ser. No. 07/988,919, filed Apr. 5, 1993, now abandoned, which is a national stage application of International Application No. PCT/EP91/01780, filed Sep. 13, 1991.

FIELD OF THE INVENTION

This invention is in the field of medical therapeutics and concerns novel means of delivering therapeutic agents. In particular, this concerns percutaneous or surgical application of therapeutic agents which are intended to remain at or near the location at which they are placed by the treating physician or surgeon.

BACKGROUND OF THE INVENTION

There are a number of problems in medicine for which therapy requires direct physical placement of a treating agent. However, the means for achieving this end are extremely limited and this end has seemed to be extraordinarily difficult to achieve.

It is often possible to deliver a drug to a specific location, such as by the injection of local anaesthetic near a nerve which must be numbed. However, most small molecules will diffuse away from their injection site, or otherwise be removed and dispersed by the actions of the bloodstream, lymphatics and other movements of interstitial fluids. In a number of situations, it is advantageous for the therapeutic agent to remain at the desired location for a much greater length of time.

It is sometimes possible to place a bead, capsule or seed with an agent at a given location, but it is very difficult to apply such localised therapy over a surface rather than at a single point. Ideally there should be a rapid and effective means for coating certain surfaces in the human body with therapeutic agents.

One such problem, well known to surgeons who specialise in the treatment of brain cancer (e.g. gliomas), arises because tumour cells infiltrate into the otherwise normal brain surrounding a gross tumour. The gross bulk of tumour is removed surgically by craniotomy, however the margins of apparently normal brain always contain sufficient numbers of tumour cells as to make local recurrence of the tumour a virtual certainty. These tumours do not metastasise, so local recurrence is generally the only type of recurrence to be expected.

To treat the small number of remaining cancer cells, chemotherapy can be given. However, even very toxic agents which cause severe toxic side-effects throughout the body have only a very slight slowing effect on tumour cell growth of gliomas. Radiation therapy may be given but, in young children, the radiation causes grievous harm to the surrounding brain and, in adults as well, there is risk of severe scarring from the radiation which can cause swelling and mass effects in large regions of the brain. Although radiation clearly slows the growth of the tumour, it is virtually impossible to deliver enough radiation to slow the tumour substantially without causing unacceptable damage to the brain. Results for treatment of brain cancer remain dismal, and life expectancy after diagnosis is measured in months with or without surgery.

One significant recent advance comes from improved methods of applying 'brachytherapy'. In some brachytherapy approaches, multiple hollow latex catheters with radioactive material in their tips are inserted into the brain, generally with computer and image-guided stereotactic methodology or by use of any one of a number of computer and image-guided spatial position wands. These catheters cause a risk of infection spreading along the catheter and do not provide a uniform field of radiation and are not well suited for treating the surface of the tumour resection bed in the brain.

In one improvement which is currently the best state of the art, the radioactive material, commonly an isotope of iodine, is enclosed in small stainless steel or titanium 'seeds' which are 0.8 mm×4.5 mm in size. Immediately after the surgeon resects the tumour, and before any surgical closure is commenced, the surgeon uses a tissue adhesive such as a cyanoacrylate-based glue to attach the seeds to the brain surface along the plane of tumour resection. A tumour which was 4 cm in diameter has a surface area of e.g. 30–40 $cm^2$ of resection bed and may require some eighty or ninety individual seeds to be glued in place, one by one, in a grid pattern with as regular a spacing as possible. Each seed has a radioactive source which treats a surrounding sphere with low level, low penetration energy for use over a long period of time until the radiation decays away over, e.g. 3–4 months. The seeds are left in place.

The problem with this current method is that the painstaking process of gluing on the seeds requires as much as an hour during which time the full operating room team (surgeon, assistant surgeon, radiation therapy treatment planner, radiation therapy technician, anaesthesiologist, scrub nurse, circulating nurse) are all required to be present and are all subject to unshielded radiation exposure.

An alternative type of glue for surgical use is termed a 'tissue glue'. This is a natural biological material that takes advantage of natural components of the human clotting system. The clotting proteins and cofactors are either extracted from donor blood, or extracted from the patient's own blood prior to surgery, or, in many cases now, extracted from the patient's own blood during the surgery itself. Typically, the glue is maintained in two components, one with fibrin protein solution and the other with e.g. the calcium solution which helps activate the clotting cascade. The two components are loaded into two separate syringes and the needle tips from the two syringes are bent to run parallel to each other so that the two tips are closely apposed. The surgeon uses a double syringe apparatus to apply the two fluids to the surface of interest simultaneously. As the two fluids emerge from the needle tips onto the tissue surface they mix and congeal. This material is used for plugging leaks in the dura membranes around the brain in order to prevent leakage of spinal fluid as well as for a wide variety of other surgical applications including the assistance of wound closure and haemostasis. Tissue glues have also been proposed as means of achieving slow controlled release of various growth factors and antibiotics.

It is not possible to suspend the seeds in either a liquid cyanoacrylate glue or in either component of a tissue glue as described above, because they would sink out of solution. It would be possible to include a variety of radioactive metal cations in chelate molecules and then dissolve these molecules in a tissue glue component; however, even for very large proteins, the tissue glue allows migration of the molecules through its interstices. Thus from the point of view of most molecules, the glue is not a glue at all, but only a matrix through which they can diffuse along with the tissue water in which they are dissolved.

SUMMARY OF THE INVENTION

In a broad aspect of the invention, a ferrite or other radiotherapeutic agent, in particulate form, is suspended in a tissue glue, suitably in the pre-mix. If a colloidal solution of, say, $\beta$-emitting ferrite is prepared in a tissue glue, this can be applied after surgical resection of a tumour, particularly near an eloquent area of the brain, where a thin shell of tumour may remain, minimising exposure to the surgeon and operating staff. The particles are biodegradable, and so will be resorbed over weeks. A cell adhesion moiety-coupled radionuclide may be used, if the agent is not physically held in the matrix.

Further aspects of the invention are indicated below and are also defined by the claims. Apparatus of the invention is illustrated in the drawings, and comprises any combination of the means illustrated for achieving the given purpose.

DESCRIPTION OF THE INVENTION

The radiotherapeutic agent may be any of a variety of nuclides, depending on the energy, penetration or half-life that is desired. Appropriate choice of such criteria is within the skill of those knowledgeable in the art. It is preferably a ferrite, e.g. a $\beta$-emitting ferrite, and preferably comprises; a chelate.

Suitable tissue glues are also known. This component may be, for example, based on a clottable protein such as fibrinogen. For example, a glue such as Tisseel (available from Immuno Danmark A/S of Copenhagen) may be used. Tissue glues, including fibrin and cyanoacrylates, are also described by, for example, Kottai et al, Ann. Otol. Rhinol. Laryngol. (1983 Jan–Feb) 92(1 Pt 1):29–32; Ronis et al, Laryngoscope (1984 Feb) 94(2 Pt 1):210–3; Barnstable, Nature (1986 Jun 19–25) 321 (6072):731–2; Toriumi et al, Otolaryngol. Clin. North Am. (1994 Feb) 27(1):203–9; and Schlag et al, in Fibrin Sealant in Operative Medicine vo. 1, G. Schlag. 11. Redl (eds), Springer-Verlag Berlin-Heidelberg (1986) 27–38.

The term "tissue glue" is used herein in its broad sense, i.e. as any tissue-compatible matrix within which the active component is retained, suitable for topical or other application to the locus of treatment. It may therefore be a gel-like substance comprising pores within which the agent is held. It will often be proteinaceous, and usually it will be biodegradable.

According to one aspect of this invention, it has been appreciated that larger particles can readily be immobilised in a variety of gels such as the tissue glue. Further, these particles are made in such a way that they can be fully and stably dissolved in water or in e.g. the calcium fluid component of the tissue glue, yet these particles are small enough to be sterilised by filtration methods along with the solution in which they are dissolved. The particles can be manufactured in such a way as to incorporate a wide variety of different metal cations, including their radioactive isotopes (to include emitters of $\beta$-particles, $\alpha$-particles, $\gamma$-rays, or X-rays from K-capture decay) in the ferrite crystal matrix at their core. The nuclides are very stably incorporated into the ceramic type core of 10–200 nanometers in diameter and the core is coated in any one of a variety of macromolecules such as dextran.

These particles can be made radioactive in several different ways. It is only necessary to dissolve radioactive isotopes of certain metals as soluble metal chlorides in the initial metal chloride solution prior to the ferrite precipitation step disclosed in WO-A-9305815 and U.S. application Ser. No. 08/211,041, filed Mar. 16, 1994, the content of which is incorporated by reference.

The isotope palladium-103 ($t^{1/2}$=17 days, EC) is extremely useful for brachytherapy with permanent implants because of its useful half-life which allows treatment of a cancer as various cells in the tumour pass into the radiosensitive cell division process over the course of days and weeks. The X-rays produced by its electron capture decay have low energy (half-value thickness in water of 1.6 centimeters) and hence it is possible to have exceedingly precise control over the area treated, as for example in the post—excision area where invisibly small amounts of tumour may have invaded surrounding normal tissue to a depth of a few millimeters. It is also the case, as is disclosed in WO-A-9211846 and U.S. application Ser. No. 08/087, 78:L, filed Jul. 7, 1993 (the content of which is incorporated by reference) that palladium is very readily incorporated into spinel ferrites in stable fashion.

Two readily available methods exist for the production of $^{103}$Pd. The first is by the use of low energy neutrons from a production reactor to irradiate the $^{102}$Pd stable isotope. It should be noted that this method has the disadvantage that $^{102}$Pd is only one of five different stable isotopes of palladium (see Table 1) and makes up only 1% of naturally-occurring palladium. For reasons discussed below, it is necessary to extract the 102 isotope prior to irradiation because of the undesirable qualities of the other resulting radioisotopes if the full mixture of stable palladium isotopes is irradiated (see Table 2). The second method for production of $^{103}$Pd is to use a high energy cyclotron capable of causing reactions with protons (conventional cyclotrons use deuterons and alpha particles which have greater mass/charge). Such an instrument can be used to irradiate rhodium which occurs naturally as only a single isotope, $^{103}$Rh, so that all conversions are to $^{103}$Pd which is then separated chemically from the rhodium in carrier free form.

Another medically useful nuclide for delivery with ferrite or other particles is yttrium-90 (t=64 hours, 1-, 2.283 MeV). This is readily produced from low energy neutron irradiation of $^{89}$Y since 100% of natural yttrium occurs in this form. The pure beta emission and half-life are suitable for such tasks as radiation synovectomy and treatment of other very thin layers of disordered tissue. The provision of $^{90}$Y in an appropriate liquid carrier has been a problem for many years since, for intra-articular use, small molecule carriers and colloids tend to leak out of the joint, while large particles do not distribute properly because they do not remain in solution. It has been suggested previously in WO-A-9211846 (see above) that various lanthanides can be incorporated into garnet ferrite-type crystals. For the inclusion of yttrium, a second period Group IIIB element, it has been appreciated that the stability and efficiency of incorporation can be improved by forcing the yttrium into a modified spinel crystal.

The prototype mineral spinel ($MgAl_2O_4$) is based on a close-packed, face-centred, cubic crystal of oxygen atoms with metal ions placed at interstitial spaces in the crystal. There are A spaces which accommodate ions of 0.3 to 0.6 angstroms (8 sites/subunit) and B spaces which accommodate ions of 0.6 to 1.0 angstroms (16 sites/subunit). In natural spinel, the divalent magnesium ions are in the A spaces and the trivalent aluminum ions are in the B spaces. Magnetite is an 'inverse spinel' because the crystal subunit of 32 $O^{2-}$ anions has trivalent $Fe^{3+}$ in the 8 A-sites, with 8 B-sites occupied by divalent $Fe^{2+}$ and 8 B-sites occupied by trivalent $Fe^{3+}$.

When $Zn^{2+}$ cations are substituted for $Fe^{2+}$ cations in the initial mixture, they tend to enter the A-sites because they are slightly smaller than the $Fe^{2+}$ cations. This forces the crystal into a 'spinel' configuration. However, as the concentration of $Zn^{2+}$ approaches 50% of the divalent cation, the crystal has steric problems because the $Zn^{2+}$ cations are still actually a bit too large for these A-sites. Above 50% $Zn^{2+}$, the crystal produced is again an inverse spinel and these effects are well studied because of their impact upon the magnetisation of bulk ferrites. An entirely unanticipated aspect of this system has been discovered, i.e. that under these conditions of flux in the crystal structure near a 50/50 mix of $Zn^{2+}$ and $Fe^{2+}$, the large $Y^{3+}$ cations are more readily accommodated in the crystal and a more stable mixed ferrite results. This may also reflect retention of partial inverse spinel structure with smaller $Zn^{2+}$ cations in enough of the B-sites to allow for additional space to accommodate $Y^{3+}$ in the B-matrix as well.

An alternative manoeuvre is to use $Li^{1+}$ cations to balance the stoichiometry when replacing $Fe^{2+}$ cations with $Y^{3+}$ cations. The Li and Y are added in equal amounts as the $Fe^{2+}$ is reduced. However, the $Fe^{3+}/Y^{3+}:Fe^{2+}/Zn^{2+}$ system produces a stable yttrium-carrying ferrite with medically useful qualities.

The incorporation of yttrium in particles for radiation synovectomy also makes possible a solution to one of the principal problems now limiting the use of this procedure. A needle is used to inject the material into the joint, but when the needle is withdrawn some of the radioactive material becomes subject to leakage out of the joint. To minimize this problem, patients are now required to remain motionless in bed in hospital for several days.

The incorporation of the radioactive yttrium into ferrites makes possible several methods of limiting the leakage and subsequent spread of radioactivity. Firstly, the knee can be wrapped in a magnetic coil which will prevent any leaked radioactive ferrites from spreading out of the area. More simply, however, tissue glues can be used to help seal the joint capsule. Because the radioactivity is incorporated in a substance which does not diffuse through tissue glue, the application of tissue glue to the injection site will prevent leakage. The half-life of the $^{90}Y$ is sufficiently short that most of the radioactivity will have decayed before the tissue glue will have broken down. In this aspect, the invention provides a system which inhibits unwanted spread of synovectomy agent.

In a further modification, the Y-ferrites may be fully incorporated into the tissue glue at the time of injection into the joint via a double-barrelled, double-needle syringe. The, say, fibrin glue is allowed to set within the involved joint, but its injection is accompanied by agents which help promote fibrinolysis, such as tissue plasminogen activator, or it is applied in a specially modified tissue glue preparation which is compounded to hold a lower concentration of fibrinogen then is usually used. In this fashion it can be assured that the ferrite-containing gel will dissolve over 2–4 days during which time much of the activity of the Y will be retained. During the breakdown process, macrophages are known to be actively attracted into the matrix and will ingest radioactive particles as well. This will thus serve as a means of both reducing leakage from the joint and effectively loading macrophages with radioactive ferrites so that when they subsequently distribute to the synovium they will be highly active.

Most effectively, the technique will involve a three-stage injection into the knee from a four-barrelled syringe. One barrel contains low fibrinogen glue component mixed with radioactive ferrites, another barrel contains the calcium solution, a third barrel contains ferrite-free fibrinogen solution, and a fourth contains radioactive ferrites in a suitable buffered aqueous medium with an X-ray contrast agent such as iohexal. After introduction of the double needle into the joint, the injection is commenced with radioactive ferrites in aqueous medium. Next the needle is partly withdrawn (under fluoroscopic guidance) to near the exit from the joint capsule, and here an injection is done to mix radioactive low fibrin glue component with the calcium solution. Finally, the needle is withdrawn to just outside the joint and non-radioactive tissue glue is then administered to fully seal the joint capsule.

It has further now been appreciated that alternative means of incorporating radioactivity in the ferrites will sometimes be useful. One such alternative method is to include in the crystal matrix an element or isotope which is the 'parent' of the desired isotope. The entire formed particle, in aqueous solution, is then bombarded with neutrons in a reactor or with protons, deuterons, or alpha particles from a cyclotron beam or nucleons from a linear accelerator in order to render the parent nuclide into the desired daughter isotope. This method has the disadvantage of causing some of the carrier iron atoms and the carbon, hydrogen, and oxygen atoms in a dextran coat to be converted to possibly undesirable isotopes as well. However, the dextran atoms are present in far lower concentration than the atoms in the particle, so the situation of the ferrite alone can reasonably considered as the greatly predominating source of post-irradiation nuclides.

There are however a variety of nuclear reactions involving iron isotopes which would typically be considered as non-productive or useless in that the resulting nuclides are themselves a mixture of stable isotopes of no medical use. It has now been appreciated, however, that in the setting of this type of ferrite carrier, the objective is properly to change carrier atoms only into different stable carrier atoms, while the therapeutic or diagnostic daughter nuclide included in the matrix results from a selectively introduced parent isotope incorporated chemically prior to the irradiation.

Such primarily stable shifting takes place in the course of low energy neutron bombardment in a reactor. Naturally-occurring stable iron is 92% $^{56}Fe$, 6% $^{54}Fe$, 2% $^{57}Fe$ and 0.3% 58 Fe. After low energy neutron bombardment, the majority of atoms ($^{56}Fe$) will be changed to $^{57}Fe$ which is just a different stable isotope and the existing $^{57}Fe$ converts to stable $^{58}Fe$. In this case however, the $^{54}Fe$ becomes $^{55}Fe$ with 2.7 yr half-life and EC capture decay, and the small amount of natural $^{58}Fe$ becomes $^{59}Fe$ with 45 day half-life and β and gamma decay. As shown in the attached Table 3, the oxygen in the crystal as well as the carbon and oxygen in the dextran are converted substantially to stable isotopes by this reaction (n,γ). If such particles are held in storage for e.g. 10 half-lives of the $^{59}Fe$, the very small starting amount will be reduced to a negligible contribution, and the resulting particles will remain as a long half-life EC capture emitter. Such a material could be useful in the fabrication of temporary implants for brachytherapy where the implant is cast in the form of seeds, catheters, or reusable, pumpable liquid for catheter-based, temporary brachytherapy.

To use low energy neutron bombardment (n,γ) for non-productive change, it would be necessary to prepare the ferrites from $^{56}$Fe-enriched iron to minimize undesired radioactive products. However, any $^{102}$Pd included in such a $^{56}$Fe-enriched ferrite would be converted to useful $^{103}$Pd ($t^{1/2}$=17 days, EC). As shown in Table 2, it is important that virtually no $^{106}$Pd be included in the starting particle for this treatment since it would be converted into a very long half-life, low energy beta-emitter ($^{107}$Pd, 6.5×10$^6$ y, β-, 0.033 MeV, decaying to stable $^{107}$Ag). However, for the preparation of permanent implants, this would be a desirable effect, and natural, mixed isotope palladium could be used as a starting material. The small amount of $^{103}$Pd produced would decay to negligible amounts after ten half-lives (170 days), after which the material could be treated as an effectively permanent source of low energy beta particles. In yet another aspect, because of the extremely low energy of these beta particles, the use of a plastic or silastic capsule or a titanium capsule around a seed cast to include such ferrites, or a thin, e.g. 1 mm, layer of ferrite-free tissue glue would provide nearly complete shielding of the beta emissions. In this way, the natural palladium ferrite could still be used as a permanent implant emitting effectively only the desirable X-rays from electron capture decay of $^{103}$Pd. The $^{109}$Pd (13h, β-,1 MeV) produced from natural $^{108}$Pd would still make it necessary to hold the particles for at least ten of these half-lives (130 hours) to reduce this beta output if it was desired to use only EC X-rays. However, in many therapeutic situations, inclusion of a 1 MeV beta particle would be useful along with the EC X-rays.

Fast neutron bombardment of Fe-enriched ferrites is another feasible means of producing useful medical isotopes via the (n,p) reaction. The various nuclides produced form the dextran-coated ferrite carrier are all very short-lived (see Table 3).

Use of a high energy cyclotron to bombard $^{56}$Fe-enriched ferrites with protons results in $^{56}$Co which is a relatively long half-life (77 days) positron-emitter. In both these cases, the advantage is in the ability to incorporate the radioactivity after the chemical preparation, clean up, and concentration steps have been completed. This avoids exposure to those involved in preparing the material and is particularly helpful in preparing positron-emitting ferrites since it is extremely difficult and awkward to shield production workers from positron annihilation photons due to their high energy.

In yet another aspect, the bombardment of $^{56}$Fe-enriched dextran-coated ferrites with alpha particles would produce $^{58}$Ni (α,2n) which is stable but would have the advantageous effect of converting oxygen atoms in the ferrite crystal as well as in the dextran into the short half-life (110 min) positron-emitter 1F (α,pn) which has a wide variety of medical uses; however, the side-reaction of (α,pn) production of $^{58}$Co (70d,β+) limits the value of this production method. Treatment of dissolved dextran by alpha bombardment prior to the precipitation reaction would cause the inclusion of F in both the dextran coat and in the interior of the crystal.

A completely different way of adding radioactivity after manufacture of the ferrites or of any other useful particle of the desired size range is to conjugate chelating groups such as EDTA, NTA or DTPA to the dextran coat of the ferrite or surface group of any other particle. In this fashion, all preparation steps are done with non-radioactive materials. Finally, when the material is to be shipped for use, or even at the site of use, the chelate-conjugated particles are exposed to dissolved radioactive metals or other chelatable elements. The elements need only have higher binding affinity to the chelate than e.g. sodium used to fill the chelate prior to radioactive uptake.

After exposure of an excess of the particles to the radioactive material, it is optionally possible to use centrifugal ultrafilters or simply passage through Sephadex columns to separate the hot particle fraction from any unbound radioactive elements.

It should also be noted that the considerations discussed above concerning palladium isotopes also apply in this alternative situation in which a reactor is used to irradiate natural mixed palladium before preparation of the ferrites in which such resulting palladium is dissolved and used to load chelator molecules conjugated to the dextran or other coat of the ferrite and additionally these considerations apply where the post-irradiation palladium is used to make radioactive Fe—Pd ferrites by precipitation from dissolved irradiated palladium chloride.

It should additionally be noted that these considerations are not restricted to the element palladium but can readily be worked out as they apply to a wide variety of medically useful nuclides when prepared for delivery in a ferrite-based particle.

Choice of the coating type and e.g. the size of dextran molecule to be used controls the final diameter of the particle. A 5,000 MW dextran coating will yield a particle more likely to migrate in a loose gel which would be preferable for drug delivery, while a 100,000 MW dextran coat would tend to produce a particle which resides very stably in the matrix for e.g. radiotherapeutic applications. Final particles can be converted to larger conglomerates by use of various conjugation reactions to create linkages between dextran molecules of multiple particles.

WO-A-9305815 and U.S. application Ser. No. 08/211,041 disclose that the particle preparation can be cleansed of any unincorporated or easily soluble cations through treatment with a chelation buffer. The buffer may comprise EDTA (ethylenediaminetetraacetic acid), DTPA (diethylenetriaminepentaacetic acid), NTA (nitrilotriacetic acid) or various other metal cation chelating agent either with or without e.g. meglumine as a counter-ion. These chelation buffers act at least in part to dissolve metal hydroxide polymers without dissolving the magnetite or other mixed metal crystal. The dissolved, chelated ions which were not properly incorporated in the particles at the time of the initial precipitation reaction are then easily separated from the particles. Originally, it had been appreciated that this manoeuvre greatly improved the simplicity of manufacture of such ferrites.

It has now been appreciated that it is important to be able to remove any radioactive nuclides which are not stably incorporated in the particles when a brachytherapy product for therapeutic use is to be made from the resulting preparation. Application of tissue glue-borne nuclides relies on a very high proportion of all the radioactive nuclide migrating stably with the particle fraction during synthesis, since only the particle-bound fraction will be held stably by the matrix in vivo. The chelation buffer step was originally described in WO-A-9305815 and U.S. application Ser. No. 08/211,041, as a means of improving the behaviour of particle solutions during filter purifications. It has now been found that this method results in a unique solution which provides an entirely novel mechanism for stably holding a variety of radionuclides stably in a matrix.

It should be appreciated that this innovation has uses not limited to tissue glues but also provides a convenient means for incorporating radionuclides into a wide variety of carriers of various types and useful for various purposes. These uses all have in common the need to hold a nuclide in place so that it is not allowed to move or diffuse or dissolve freely through the medium or carrier into which it has been introduced.

Any particle can contain a range of nuclide concentrations ranging from one atom per crystal, up to e.g. 100,000 or more atoms per crystal. This choice allows both for storage of the particles over the long term and for a wider choice of possible isotopes to be used depending upon the therapeutic task to hand. Groups of particles can also be conjugated together with periodation reactions or glutaraldehyde reactions in order to make them larger in the aggregate so that they achieve greater stability in looser gel matrices.

It should also be appreciated that this means of particle application is not restricted to tissue glue alone, but also applies to various other collagen matrices or other matrix or gel-forming substances tolerable for biological use or foams or gelfoam substances as well as with a wide variety of other adhesive materials which can be used to hold particles and keep them at a chosen proximity to a particular target.

When fibrin-based tissue glue is used as the matrix for immobilizing the particles of whatever type, the function of the invention will be greatly affected by the stability or rate of breakdown of the tissue glue matrix. Fibrin tissue glue is subject to breakdown from the action of natural fibrinolytic proteins. The amounts and concentrations of these fibrinolytic proteins vary from tissue to tissue within the body. On average, a tissue glue layer in the human body would be expected to lose the greater part of its physical integrity within a period of about 10 days from application. In many cases this is desirable, however in other cases it may be desirable to either extend or shorten the period of stability of such a gel. In the case of fibrin glues, there is a variety of proteins and other agents well known to affect the natural metabolism of fibrin clots. These agents have been used for a variety of purposes but have not been considered as a means of manipulating the drug delivery properties of gels or as a means of controlling radiotherapy or gene therapy.

One such agent is amicar (ε-aminocaproic acid). A typical use is to slow the breakdown of clots which form on ruptured cerebral aneurisms and so to inhibit their risk of repeat haemorrhage. If amicar or similarly acting agents such as aproteinin or various proteinase inhibitors are incorporated in the gel matrix, either simply by mixing them into the initial solution or by adhering or conjugating them to particulates intended to be included in the matrix, then these will slow the breakdown of the gel. Alternatively, the inclusion of agents such as tissue plasminogen activator or streptokinase will speed the breakdown of the gel.

Prolongation or shortening the stability period of gels has not previously been considered in relation to the use of tissue glues for drug delivery. This is because all previous descriptions of the use of tissue glue for drug delivery have involved drugs which diffuse out of the gel matrix fairly rapidly so that the length of time of survival of the gel has little impact on the rate of delivery. However, in the current invention, many of the aspects of the drug delivery mechanism are closely dependent upon the rate of tissue glue breakdown.

In one aspect, a locally active protein which would benefit from slow release, such as bone matrix protein, is conjugated to a particulate such as the dextran-coated ferrite. Many such proteins will retain their physiologic activity even though they are conjugated to a particle. The clinical problem is to provide slow release of the protein from the gel. By immobilizing the protein/particle conjugate in the gel, the physiologic activity is delayed until the matrix is physically degraded. Here the particle acts as an anchor and the breakdown of the gel releases the anchor.

In another aspect where tissue glue is used to hold a $^{103}$Pd ferrite for brachytherapy, the half-life of the nuclide requires a relatively long period of stability of the gel in order to minimize spread from the site of application prior to the passage of three to five half-lives. In tissues such as prostate with high concentrations of fibrinolytic proteins this a particular concern. Although a variety of longer-lasting synthetic and semi-synthetic gels can be used, the addition of an anti-fibrinolytic allows the use of fibrin tissue glue.

Yet another application is in the treatment of arteriovenous malformations in the brain. Currently these are treated non-surgically either by using intravascular catheters to fill the vessels with an occluding matrix or by external beam therapy. In this invention, a tissue glue may be injected with radioactive ferrites ($^{103}$Pd or $^{90}$Y). This would allow for simultaneous embolization and radiation sclerosis of the AVM vascular walls. Prolonging the life of the tissue glue would help assure focal delivery as well as prolonging the life of the embolic vessel blockage. If the interventional radiologist found that too much vessel had been blocked, then fibrinolytics could be applied to rapidly dissolve the gel and allow the radiation to diffuse through the body where it would be present in extremely low concentration because of the large volume of distribution relative to the amount of radioactive agent involved. The ferrites could also be collected from the blood stream by a magnetic filter.

In order to localise therapeutic agents, various means involve tissue glue. One is based on physically conjugating a variety of carrier proteins directly onto the fibrin in the tissue glue. The conjugation can be carried out through antibodies to the fibrin or through the use of periodate conjugation. The carrier proteins and dextran molecules incorporate chelate molecules in a variety of arrangements all well known to those expert in the art of therapeutic metal ion delivery. Additionally, this includes non-metal therapeutic radionuclides attached in other ways. By way of example, the radioactive iodine may be conjugated directly to the fibrin by standard iodination reactions. In this fashion, the radioactive iodine or other radioactive element can be rapidly attached to the patient's own proteins for use in autologous tissue glue.

It is also now appreciated that in addition to radiotherapy applications, these particles applied by tissue glue may be used to deliver a variety of other locally useful therapeutic agents. It is possible to adhere nucleic acids onto these particles as disclosed in WO-A-9305815 and U.S. application Ser. No. 08/211,041. It is now also appreciated that in addition to genes, it is possible to adhere anti-sense oligonucleotides.

It is now known that gliomas involve a defect in a gene termed the p53 gene and that this defect can be corrected by gene therapy, however there is no known way to deliver the therapeutic genes to the glioma cells (abnormal astrocytes). It is now disclosed that therapeutic genes for the treatment of brain tumours may be adhered to the surface of the particles and the complex then included in a liquid component of the tissue glue. The glue is then applied at the time of surgery to the excision surface.

Astrocytes are phagocytic cells and have been demonstrated to avidly take up these particles into their interior, while neurons are far less phagocytic. By using smaller particles and a looser matrix, the particles may be allowed to migrate slowly out of the matrix into the nearby or surrounding brain and to there be ingested by the actively phagocytic astrocytes. This may be further promoted by the use of targeting proteins or antibodies which adhere to the surface of astrocytes generally or which may be targeted to markers expressed in excess amounts by cancerous astrocytes. These targeting proteins may be adhered to the particle surface by chemical conjugation by the periodate method, or by a variety of other adhesion or conjugation methods well known to those skilled in the art.

It is further appreciated that nucleic acids may simply be incorporated into these glues by mixture without using these particles as carriers. Where particles are used as carriers, a variety of types of particles is suitable, including cyanoacrylates, liposomes, albumin or other protein-based materials, starburst dextran dendrimers, starches, pectins, polylysine or other polymers.

Further, it has now been appreciated that viruses of sizes similar to the particles can also be immobilised in tissue glues. Thus, the therapeutic genes delivered by the glue can be carried in retroviral vectors such as those described in WO-A-9317118 and U.S. application Ser. No. 08/295,737, and also PCT/GB95/00663. The admixture of retroviral and other viral vectors into one component of a tissue glue or settable matrix has a wide variety of applications where selected local gene therapy is desired. The viruses gain access to cells either by slow release from a loose matrix or by release associated with biodegradation of the gel matrix.

Alternatively, a loose gel may be used to immobilise cells infected with retroviral or other viral vectors or 'producer' cell lines containing all the genetic material needed to produce viral particles and a vector molecule for encapsidation therein. The cells are held in place by the matrix, but the viral particles pass through the loose gel for the purpose of transfection or gene therapy. These immobilised cells can be used for local delivery of viral vectors or for delivery of vectors into the bloodstream for action at a distant site. Genetically-modified cells trapped in a tissue glue can also be used as sources of therapeutic proteins which will then diffuse out of the gel after production in the modified implanted cells as with various growth factors, hormones, neurotransmitter modulating enzymes, antibodies, or cytokines.

In addition to the use of these particles for radiotherapy and for the delivery of genes, they may be used as transducers for the application of hyperthermy treatments. After placement of a ferrite particle containing gel, the patient may be exposed to oscillating electromagnetic fields tuned to the particle type of particle used. Thus the particles can be caused to become hot and so provide a controllable heat therapy either separate from or in conjunction with their radiotherapeutic effect.

In addition to the potential for carriage of macromolecules, emission of radiation and transduction for heating, these particles can also be used as a means of delivering cation therapy, as disclosed in WO-A-9211846 and U.S. application Ser. No. 08/087,781 (see also above). In this system, various non-physiological cations are incorporated into the crystal matrix of the ferrite core. The particles are then delivered in a tissue glue. Subsequently, as the glue breaks down or as the particles slowly leach out and are ingested by various cells, the cations are released through intracellular metabolism of the iron oxide core. Delivery of cations can be used for the treatment of viral illness and also for cancer chemotherapy.

This antibiotic effect may also be exploited in a variety of hard coatings into which these particles may be incorporated. Where various cations offer anti-bacterial effects, these may used in coatings on e.g. various implants.

Additionally, the radiotherapeutic tissue glue can be augmented by the inclusion of synergistically acting diffusible drugs, either loosely incorporated in the gel for free diffusion or introduced in semi-soluble or insoluble form in order to achieve slow release, or weakly adhered to the dextran or other polymer coating of particles. Such particles serve to temporarily immobilize and control the distribution of such drugs. Radiotherapy can interfere with wound healing in some situations. It will therefore often be advantageous to counter the anti-wound healing effects of radiation by the inclusion of various growth factors in the gel as disclosed in WO-A-9420133 and WO-A-9209301. Further, it may be possible to assist the anti-cancer effect of the radiation by inclusion of a variety of chemotherapeutic radio-sensitizer drugs or actual chemotherapeutic agents in the gel along with the radioactive source.

In addition to the various gels and glue carriers mentioned above, it should be appreciated that the radiotherapeutic particles, particularly the EDTA-insoluble particles, can be dissolved in aqueous-based plastic polymers which can then be caused to polymerize in the same fashion as described above for the tissue glues. The additional feature of a plastic is that it would allow for casting of a sealable shaped radiation carrier prior to surgery or during surgery.

Figure 1:
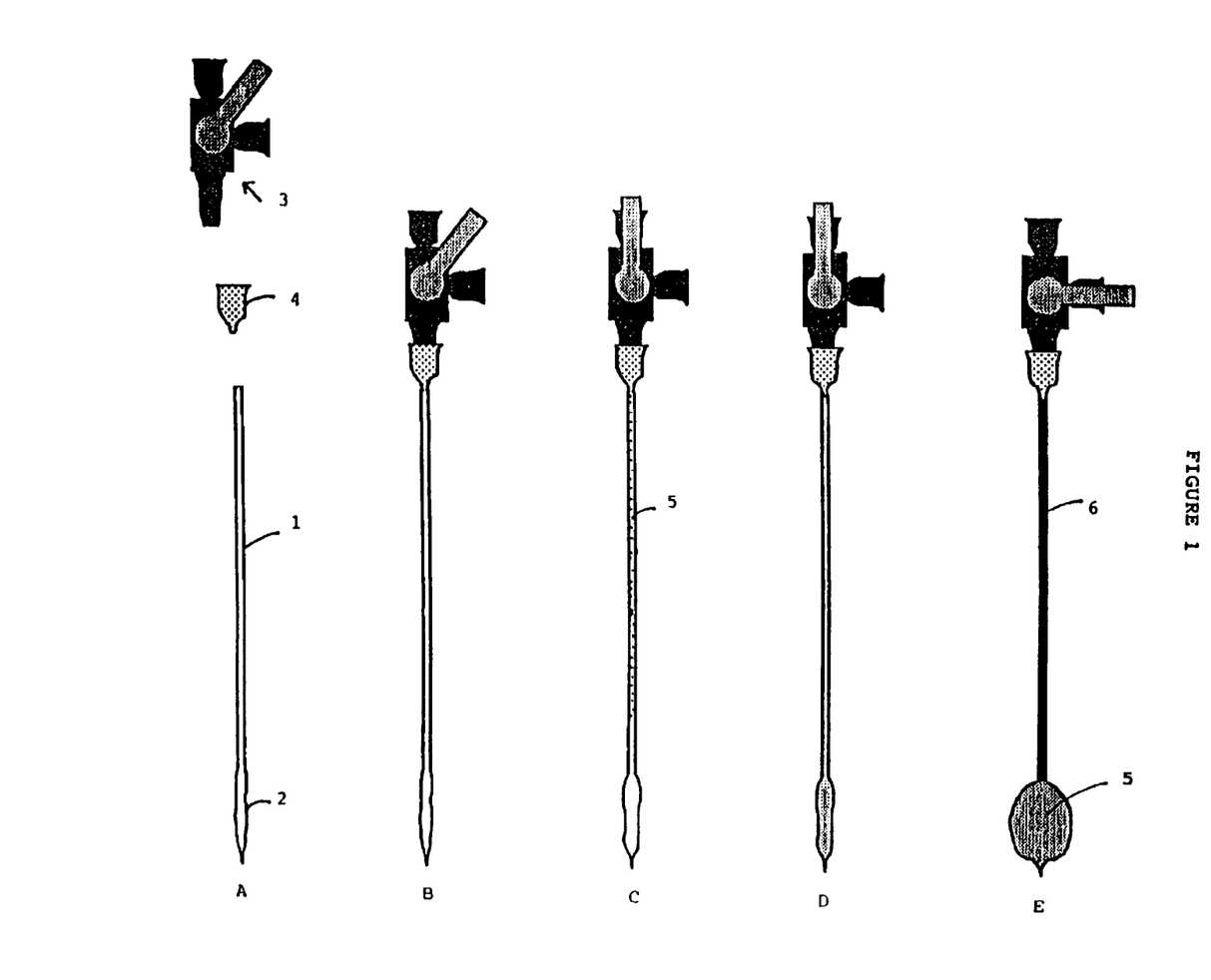
FIG. 1 shows a balloon-tipped catheter system, for temporary introduction of liquid brachytherapy agent, including a catheter 1, collapsed balloon tip 2, stopcock 3, an adapter 4, radiotherapeutic liquid 5 and an immiscible 'chaser' fluid 6.

Yet another means of administration of the radiotherapeutic particles is in liquid form in association with specialised catheter systems which may or may not be further associated with endoscopic equipment. This could be for a temporary application of radiotherapy. For example, in the case of the need to treat a localised lesion in a bronchus of the lung, the therapist would endoscopically introduce a very thin catheter with a much larger diameter balloon tip. At the time of introduction the catheter would be completely collapsed by withdrawal of air and subsequent turning of an external sealing valve. Once the tip was positioned correctly, the radiotherapeutic liquid would be pumped into the catheter. Where the catheter is very thin, there will be only a very low dose of radiation to surrounding normal tissue, however, a large amount of the agent would accumulate in the balloon tip and administer large amounts of radiation at that site (see FIG. 1). The volume of the catheter system and of the balloon tip can be precisely known so that only enough radiotherapeutic agent to fill the balloon tip is pumped in. Then an immiscible liquid (e.g. paraffin oil) is pumped into the catheter as a chaser so that all of the radioactivity will be in the balloon tip and only cold chaser oil will be in the thin feeder catheter where it traverses normal tissues. The catheter is fashioned of a plastics or other non-wettable material on which water beads readily and hence the oil is efficacious at substantially sweeping all the radioactive aqueous material distally towards the balloon.

In some situations, it will be desirable simply to introduce the liquid form of the brachytherapy agent (e.g. with palladium-103) into the tissue around the site of tumor excision. These particles are preferentially cleared into and concentrated in lymph nodes. Similarly, an early stage in the spread of cancer away from its initial site is along the lymphatics where it is initially trapped in lymph nodes. The brachytherapy agent may be selectively concentrated in local lymph nodes and provides an additional selectively beneficial effect in preventing and treating any early spread of tumour cells. This is particularly important immediately after a surgical resection at which time numerous individual tumour cells are spilled by the surgeon in the process of physically mobilising and removing bulk tumour. These free floating tumour cells in the excision site are often cleared to lymph nodes where they can proliferate and to cause recurrence.

A solution of the particles may be aerosolized for spray application to a surface in the body in a system in which the spray forms part of a tissue glue which sets upon contact. Similarly, an aerosol route can be used with the liquid agent without glue for diffuse application in the bronchi or via the GI tract. An aerosol spray of the particle-carrying liquid can also be used to apply a thin layer of the particles in an even fashion to a sheet of implantable material. That sheet may then be sealed with a thin additional plastic layer. The inclusion of the elements in the nanoparticles will assure that radioactive elements will not diffuse through the pores of the plastic.

For applications such as cation therapy where containment is less of a concern, the tissue glue may be applied by spray-on application. An antibiotic fluid may be incorporated in the vehicle against any airborne contamination. In the spray-on methods, the fluid vehicle will either be so prepared as to polymerize in air, or two separate sprays may be used, first a carrier for the fibrin portion followed by the calcium and particle component. These applications may be from a pressurised can or from a simple standard nebulizer.

In order to apply the therapeutic tissue glue in applications where a layer must be applied to a surface, several specialized devices for this purpose may be used and are herein disclosed. Instead of two needles ending in a point, the exits from the two application syringes are so fashioned that at their termini they widen into a flat applicator. The two channels are laid one over the other and attached to each other so that both deliver a sheet rather than a stream of glue components (see FIG. 2) and these two sheets mix on exit, resulting in a sheet of controlled depth on the tissue surface. Each applicator kit can be supplied with several of these applicators so they may be readily replaced if they become clogged through premature mixing of the two components. These sets of applicators may be provided in a series of widths including, e.g. 5, 10 or 20 mm, which may be selected based on the size and shape of the surface to be coated.

Figure 2:
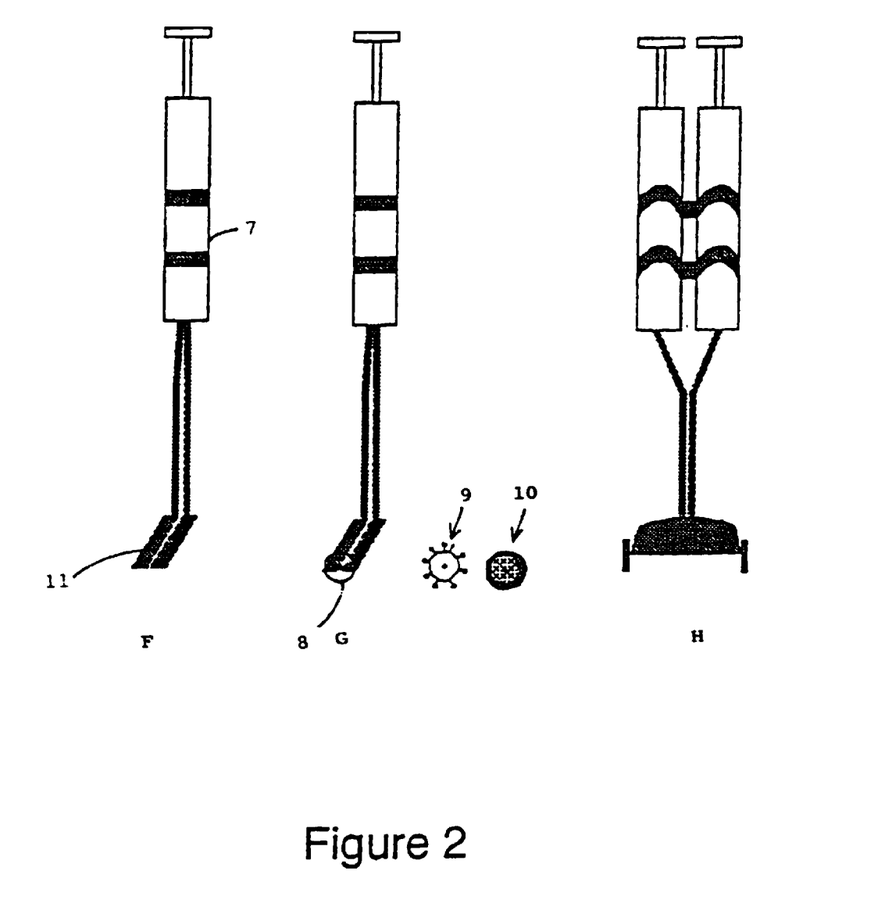
FIG. 2 shows a lead-shielded double-syringe device for applying a thin sheet of radiotherapeutic tissue glue. The syringes include barrels, one indicated at 7, a wheel 8 placed between the terminal portions of the dispenser plates to maintain a uniform distance from the tissue surface, an optional wheel 9 with penetrating feet, an optional wheel 10 with a thin silastic outer rim, and two dispenser plates 11 seen in lateral view, one behind the other.

Further, in order to control the depth of the layer of the material, the applicator may be provided with paired wheels. The wheels may either have latex rims or small feet so they do not produce furrows in the layer of the glue. The applicator may also be automated or semi-automated so that as the surgeon rolls the applicator along the surface the device measures the rate of progression from the wheel turning and then automatically drives the two syringes to apply the layer of glue. Alternatively, as the surgeon presses the syringe, the advance of the plunger may mechanically cause the wheels to turn so that the device advances over the tissue surface at the appropriate rate.

In addition to painting a layer of this therapeutic tissue glue onto the brain surface or onto the surface of any body tissue possibly invaded by cancer cells, it is also possible to inject a column or deposit of the glue in a fashion similar to the catheter arrays used for brachytherapy, but in which a column of tissue glue incorporating radioactive nuclides in particles is incorporated. Such administration can be monitored by concurrent imaging techniques which take advantage of the inherent imagability of the these particles (due to the density and magnetism of the iron core) by ultrasound, magnetic resonance imaging, or X-ray based techniques, or the gel can be supplemented by an additive contrast agent.

Similarly, injection techniques can be used to inject settable, ferrite or other particle-containing gel into the centre of the tumour mass for purposes of brachytherapy, either with or without the inclusion of chemical or biological agents capable of causing either increased radiation sensitivity or capable of acting as chemotherapeutic agents in their own right, to achieve a multi-modal attack on the cancer cells. Administration in this manner can also be achieved by injecting the glue with radioopaque material but without the ferrite/particle solution, using two barrels/needles from a three-part syringe system. Then, once the position, shape, and setting of the glue are confirmed, the third barrel/needle can be used to inject the particle solution into the centre of the matrix/glue material which will hold the material within its interstices. The needle is then very slowly withdrawn along with the injection of additional glue, to seal the needle tract.

Any such one, two, or three-barrel system for administration of glue-based radiotherapy products may be equipped with a release mechanism for detaching a plastic or silastic inside layer at the tip of the needle. This is provided in case the column of glue becomes adherent to the tip of the needle and allows the operator to choose to leave the plastic behind in the needle tract to avoid pulling out the column of glue as the needle is withdrawn. Alternatively, this problem can be avoided with a more standard glue application system as long as a chaser of cold glue is use to follow the injection of radioactive glue.

Figure 3:
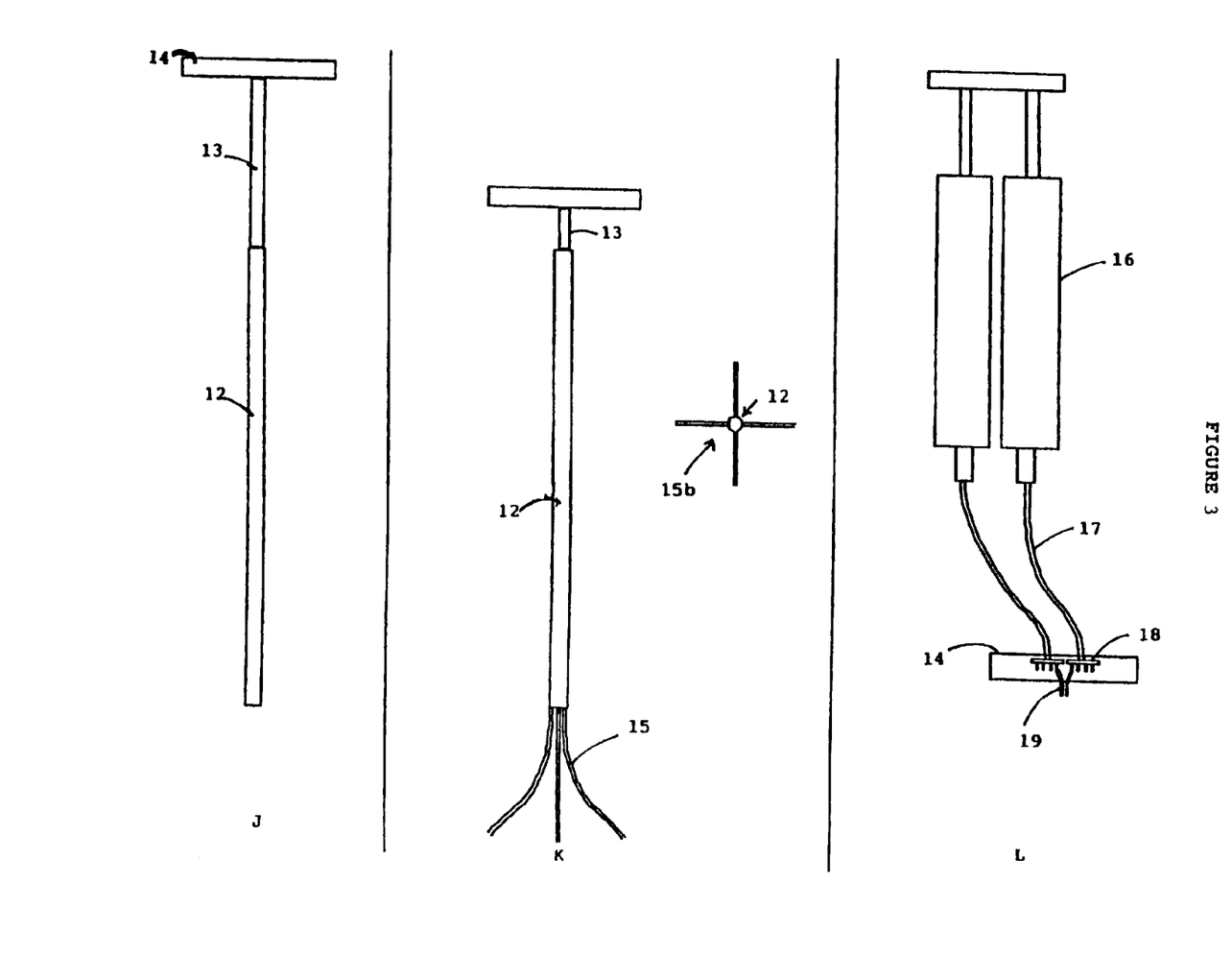
FIG. 3 shows a device for distributing therapeutic adhesive within a tumor mass, including a sheath 12, a plunger shaft 13, a plunger/manifold cover 14, needles 15 (at 15b, viewed from above with four double-barrelled needles extended), double-barrelled syringe 16, connecting tubing 17 for carrying glue components to a manifold 18 dividing barrelled needle sets out into the tumor in various directions.

In many situations, it will be desirable to inject the radiotherapeutic glue in an array which distributes the therapeutic material through the mass at a variety of locations. An example of this occurs when a stereotactic system is used to allow a neurosurgeon to place a needle or catheter into the middle of a brain tumour by passing through a burr hole in the skull. Because of the need to traverse brain tissue, it is undesirable to make numerous needle passes in order to reach multiple sites in the tumor. It has now been appreciated that a novel type of administration device would solve this problem as well as similar problems arising in other body regions where bulk tumor is to be treated. The system (see FIG. 3) involves an outer sheath of a hard material such as steel, titanium or plastics which carries a plurality of internal flexible needle pairs which are prestressed to spread outwards from the tip of the sheath. The needle pairs are withdrawn within the sheath while the tip of the sheath is advanced into the tumor. The internal set of needle pairs is then advanced, upon which their tips emerge from the sheath and spread in various directions and so puncture the tumor from inside towards the outside in various directions. Once at their full extent, injection is commenced as the needles are withdrawn back into the sheath. The internal apparatus can then be rotated, e.g. 45° and then advanced a second time. After being withdrawn into the sheath again, the sheath may then be advanced further into the tumor upon which the internal needle are again advanced.

The following Example gives the steps to be taken in an illustrative synthetic method for particles to be included in a matrix.

EXAMPLE

Add 1.5 ml of 33% $NH_3$ to 4.5 ml of hot $dH_2O$ (to make up 7.5% $NH_4OH$) and leave standing in a capped universal tube in the water bath and bring to 60° C.

Dissolve 1.25 grams of Dextran (MW 10,000) in 2.0 ml of $ddH_2O$ then dissolve 225 mg $FeCl_3.6H_2O$ in the dextran solution. Other macromolecules such as proteins, fibrin, collagen, starch, polylysine, or derivatized dextrans may also be used for the coating. Alternatively, a trivalent lanthanide or Group IIIB chloride may be substituted for 10–50% of the $FeCl_3$. A variety of unstable isotopes of various transition, lanthanide and actinide elements can be introduced at this step as metal chlorides dissolved in water or in an acidic solution of e.g. 0.1M HCl. The amount of trivalent iron may be reduced where trivalent cations are added.

Dissolve 100 mg $FeCl_2.4H_2O$ in the $Fe_3$/dextran solution then place the mixture in a 60° C. water bath for two minutes. Some divalent cations may be added in place of Fe at this step. Some metal chlorides such as, e.g. palladium chloride will require an extended period of time up to e.g. one to two days in concentrated HCl in order to become fully dissolved prior to mixing with the other constituents. When trivalent lanthanides are used, the crystal structure may be modified by the use of copper or magnesium as the divalent cation instead of the $FeCl_2$, or other stable combination of cations such as $FeCl_2$ with $ZnCl_2$ may be used to help accommodate Group IIIb elements such as the $yttrium^{90}$ isotope. Further, the reaction mixture may be allowed to stand at room temperature or be cooled as low as 0–4° C. prior to proceeding depending upon the desired size distribution of the resultant particles where cooler reaction temperatures; tend to produce smaller particles.

Gradually add 6 ml of hot 7.5% $NH_3$ solution (60° C.). The $NH_3$ solution may also be added at lower temperatures, e.g. 0–4° C. or room temperature. Equivalence of temperature and mixing to assure uniform concentration as well as more gradual and dispersive addition of the $NH_3$ solution will help reduce the range of particle sizes. The product is left to stand in the 60° C. water bath for fifteen minutes for Fe/Fe particles, but the incubation may be extended up to four hours when lanthanides or Group IIIB elements in substantial amount are used in place of $FeCl_3$.

The reaction product (dextran-coated ferrites) is spun at 1,000 g for 10 minutes and any precipitate is discarded. This process is repeated to complete three spins and the supernatant then applied to PD-10 columns equilibrated with 0.1M Na Acetate buffer pH 6.8 with 5 mM EDTA.

The black eluted fraction is diluted 1:3 with EDTA/Acetate buffer then concentrated to 1/10 of the initial volume with Amicon Centriprep-100 ultrafilters. The retentate is then diluted 1:10 with EDTA/Acetate buffer then concentrated to a volume of 1.5 ml with the C-100 ultrafilters.

At this point the preparation may be stored or further concentrated. If it is to be used with a tissue glue, it can be mixed with one component of the fibrinogen, fibrin, collagen, acrylic, gelatin, resorcinol or other type of tissue glue, matrix, or polymer precursor prior to application and mixing of the glue to set on the tissue surface.

When it is desired to attach an additional ligand such as for instance an antibody, lectin, or other agent which promotes adherence to the glue matrix, the following steps as well as other methods well known to those expert in the art of conjugation to dextran may be used.

Add 0.30 ml of 20 mM $NaIO_4$ to the dextran ferrite solution (approx. 1.5 ml) while stirring then gently tumble or shake for 60 minutes at room temperature in the dark.

At the end of the 60 minute periodate incubation, the reaction is terminated by applying the reaction mixture to the PD-10 columns equilibrated with 22 mM borate buffer (pH 8.5).

An active site blocking solution is prepared using 100 mM $MnCl_2/CaCl_2$ for WGA binding reactions and appropriate blocking agent for any other targeting protein to be conjugated to the particle.

Dissolve 10 mg of the protein (e.g. cell targeting protein or antibody) in 500 µl of 20 mM NaBorate buffer pH 8.5 at room temperature. The protein solution can be diluted to 12 ml with borate buffer, then concentrated with Centriprep-10 concentrators to remove DTT, glycerol, $NaN_3$ and other undesirable storage additives.

Add 10 µl of the blocking solution to the protein/borate solution then mix 2.0 ml of oxidized magnetite dextran with 500 µl of the protein/borate solution. Pipette 21D µl blocking solution into the 2.5 ml protein-dextran-magnetite mixture and mix well, then incubate for 6–18 hours at room temperature in a gentle tumbling or shaking device.

After the incubation add 100 1 of 0.5M glycine to the reaction mixture and incubate an additional 2 hours. Then add 250 µl of 0.25M $NaBH_4$ to the magnetite-dextran-protein solution and allow to stand for 60 minutes, shaking periodically to release $H_2$ gas. At the end of the incubation, pass the reaction mixture through PD-10 columns equilibrated with 20 mM HEPES buffer, pH 7.4. Dilute the eluant 1:5 with HEPES buffer then concentrate with Centriprep-100 ultrafilters.

An affinity purification step is optional and detail is given for use with a WGA(lectin) targeting protein by example. Apply final retentate to affinity columns (20 mM HEPES), wash with HEPES then carry out specific elution with 1M NAcGlu in HEPES buffer pH 7.4. Pass the specific eluant through PD-10 columns equilibrated with HEPES to remove NAcGlu, Mn and Ca.

The desalted output is then diluted to a volume of 24 ml with HEPES buffer and concentrated with Centriprep-100 concentrators. The final retentate form is sterilized by spinning at 500 g for one hour in 0.22 µm centrifugal microfilters.

BRIEF DESCRIPTION OF THE DRAWINGS

FIG. 5A shows the parts of the system; the four stages of its use are: B) the assembled system with air evacuated from the catheter and balloon, both being collapsed, the stopcock valve maintaining a seal, C) a column of radiotherapeutic fluid being pumped into the catheter, D) the fluid reaching and starting to fill the balloon tip, E) the balloon tip fully filled with radiotherapeutic liquid and non-radioactive immiscible chaser fluid filling the catheter up to the balloon entry point. Optionally, a second tube may be used to fill an internal balloon, or the first tube used to send down a leading column of fluid to dilate an internal balloon with the purpose of creating a thin shell of radioactive fluid against the inner surface of the outer balloon.

FIG. 2F is a lateral view of the system without the spacing wheel; FIG. 2G is a lateral view of the system with one of the optional wheels in place, and FIG. 2H is an anterior view of the assembled double-syringe system showing the appearance of one of the various widths and shapes of disposable dispenser plates which may be affixed to the syringe system.

FIG. 3L shows the syringe manifold system which allows distribution of the two component glue into the double-barrelled needles after they are in place and while they are being withdrawn.

TABLE 1

Relevant Stable Nuclides $_6$C 12(98.9%), 13(1.1%)
$_8$O 16(99.76%), 17(0.04%), 18(0.2%)
$_{25}$Mn 55(100%)
$_{26}$Fe 54(6%), 56(92%), 57(2%), 58(0.3%)
$_{27}$Co 59(100%)
$_{28}$Ni 58(68%), 60(26%), 61(1%), 62(4%)
$_{38}$Sr 84(.6%), 86(10%), 87(7%), 88(82%)
$_{39}$Y 89(100%)
$_{40}$Zr 90(51%), 91(11%), 92(17%), 94(18%), 96(3%)
$_{44}$Ru 96(5%), 98 (2%), 99(12%), 100(12%), 101(17%), 102(32%), 104(18%)
$_{45}$Rh 103(100%)
$_{46}$Pd 102(1%), 105(22%), 106(27%), 108(26%), 110(11%)
$_{47}$Ag 107(52%), 109 (48%)

TABLE 2

| Pd | n,γ | n,p | α,2n |
|---|---|---|---|
| 102 | 103Pd (17d,EC) | 102Rh (2.9y,EC) | 104Cd (58m,EC) |
| 105 | 106Pd (stable) | 105Rh (35h,β−) | 107Cd (6h,EC/β+) |
| 106 | 107Pd (10⁶y,β−) | 106Rh (29s,β−) | 108Cd (stable) |
| 108 | 109Pd (13h,β−) | 108Rh (17s,β−) | 110Cd (stable) |
| 110 | 110Pd (stable) | 110Rh (3s,β−) | 112Cd (stable) |

TABLE 3

| Cyclotron | Reactor |
|---|---|
| (p,n) | (n,γ) |
| $^{56}$Fe -> $^{56}$Co (77d, β+) | $^{56}$Fe -> $^{57}$Fe (stable) |
| $^{16}$O -> $^{16}$F (10$^{-20}$s, p) | $^{16}$O -> $^{17}$O (stable) |
| $^{12}$C -> $^{12}$N (11 ms, β+, α) | $^{12}$C -> $^{13}$C (stable) |
| $^{103}$Rh -> $^{103}$Pd | $^{102}$Pd -> $^{103}$Pd (17.5d, EC) |
|  | $^{89}$Y -> $^{90}$Y (64h, β−) |
| (d,n) | (n,p) |
| $^{56}$Fe -> $^{57}$Co (271d, EC) | $^{56}$Fe -> $^{56}$Mn (2.6h, β−) |
| $^{16}$O -> $^{17}$F (64s, β+) | $^{16}$O -> $^{16}$N (7s, β−, α) |
| $^{12}$C -> $^{13}$N (9min, β+) | $^{12}$C -> $^{12}$B (.02s, β−, α) |
|  | $^{90}$Zr -> $^{90}$Y (64h, β−) |
| (α,pn) |  |
| $^{56}$Fe -> $^{58}$Co (70d, β+) |  |
| $^{16}$O -> $^{18}$F (109min, β+) |  |
| $^{12}$C -> $^{14}$N (stable) |  |
| $^{88}$Sr -> $^{90}$Y (64h, β−) |  |
| (α,2n) |  |
| $^{56}$Fe -> $^{58}$Ni (stable) |  |
| $^{16}$O -> $^{18}$Ne (1.7s, β+) |  |
| $^{12}$C -> $^{14}$O (70s, β+) |  |
| $^{101}$Ru -> $^{103}$Pd |  |

We claim:

1. A composition comprising a tissue glue and, in particulate form, a radiotherapeutic agent or an agent convertible to a radiotherapeutic, wherein said agent mediates localized radiotherapeutic activity when immobilized in the glue.

2. The composition according to claim 1, which additionally comprises a material that inhibits degradation of the glue.

3. The composition according to claim 1, wherein the agent is in the form of a chelate holding a radioactive atom.

4. The composition according to claim 1, wherein the agent is a ferrite.

5. The composition according to claim 1, which additionally comprises a radiation sensitizer capable of leaching out and augmenting the local radiotherapeutic effect.

6. The composition according to claim 1, which additionally comprises a growth factor or other substance that mitigates the anti-wound-healing effect of radiation.

7. The composition according to claim 1, wherein the agent comprises a zinc-substituted yttrium ferrite, or a $^{56}$Fe-enriched ferrite.

8. The composition according to claim 1, wherein the agent comprises $^{103}$Pd or $^{90}$Y.

9. The composition according to claim 1, further comprising an antibody, and wherein the tissue glue is a fibrinogen tissue glue.

10. The composition according to claim 9, wherein the particulate radionuclide is a β-emitting ferrite.

11. The composition according to claim 9, wherein the particulate radionuclide is coupled to the antibody.

12. The composition according to claim 11, wherein the antibody is a nerve adhesion molecule.

13. A composition comprising a tissue glue and, in particulate form, a radiotherapeutic ferrite or a ferrite convertible to a radiotherapeutic, wherein the ferrite mediates localized radiotherapeutic activity when immobilized in the glue.

14. The composition according to claim 13, wherein the ferrite is a β-emitting ferrite.

15. A composition comprising a tissue glue and, in particulate form, a radiotherapeutic agent or an agent convertible to a radiotherapeutic, wherein the agent comprises a zinc substituted yttrium ferrite or $^{56}$Fe-enriched ferrite, wherein said agent mediates localized radiotherapeutic activity when immobilized in the glue.

16. A composition comprising a tissue glue and, in particulate form, a radiotherapeutic agent or an agent convertible to a radiotherapeutic, wherein the agent is a ferrite comprising $^{103}$Pd or $^{90}$Y, and wherein said agent mediates localized radiotherapeutic activity when immobilized in the glue.

17. A method for making a radiotherapeutic composition according to claim 9, which comprises:
    (a) preparing a particulate radionuclide; and
    (b) mixing the particulate radionuclide with the fibrinogen tissue glue and the antibody.

18. A method of using a radiotherapeutic composition according to claim 9, which comprises applying the composition directly to tumor tissue.

19. A method of radiation synovectomy which comprises administering an effective amount of a composition of claim 1 to a patient to be treated.

20. A method for the radiotherapy of a tumor, which comprises applying to the tumor an effective amount of a composition as defined in claim 1.

21. The method of claim 20, wherein the radiotherapy of a tumor comprises brachytherapy.

22. A method of radiotherapy in the treatment of arteriovenous malformations in a blood vessel which comprises applying to the blood vessel a composition as defined in claim 1.

* * * * *

UNITED STATES PATENT AND TRADEMARK OFFICE
CERTIFICATE OF CORRECTION

PATENT NO. : 6,919,067 B2
DATED : July 19, 2005
INVENTOR(S) : Aaron Gershon Filler and Andrew Michael Lindsay Lever It is certified that error appears in the above-identified patent and that said Letters Patent is hereby corrected as shown below:

Column 3,
Line 32, "comprises; a" should read -- comprises a --.

Column 4,
Lines 22-23, "08/087,78:" should read -- 08/087,781 --.
Line 46, "t=64 hours, 1-, 2.283 MeV" should read -- $t^{1/2}$ =64 hours, β-, 2.283 MeV --.

Column 5,
Line 55, "the Y-ferrites" should read -- the $^{90}$Y-ferrites --.
Line 65, "the Y will be" should read -- the $^{90}$Y will be --.

Column 7,
Line 31, "of Fe-enriched" should read -- of $^{56}$Fe-enriched --.
Line 51, "1F" should read -- $^{18}$F --.
Line 56, "of F in" should read -- of $^{18}$F in --.

Column 15,
Lines 21-22, "temperatures; tend" should read -- temperatures tend --.
Line 57, "22 mM" should read -- 20 mM --.

Column 16,
Line 3, "21D $\mu$1" should read -- 20 $\mu$l --.

Column 16, line 67 to Column 17, line 1,
"manifold 18 dividing barrelled needle" should read
-- manifold 18 dividing flow of glue components into four sets and then pairing up the sets of double-barrelled needles, one pair of needles shown at 19 emerging from manifold cover to enter the plunger shaft, and, shown at 20, a fully-extended set of double-barrelled needles spreading out from sheath tip to penetrate tumor in various directions. Fig. 3J shows the plunger lifted to withdraw needles back into the sheath. Fig. 3K shows the plunger advanced to force the four double-barrelled needle sets --.

UNITED STATES PATENT AND TRADEMARK OFFICE
CERTIFICATE OF CORRECTION

PATENT NO. : 6,919,067 B2
DATED : July 19, 2005
INVENTOR(S) : Aaron Gershon Filler and Andrew Michael Lindsay Lever It is certified that error appears in the above-identified patent and that said Letters Patent is hereby corrected as shown below:

Column 18,
Lines 23, 25 and 50, "radionucide" should read -- radionuclide --.

Signed and Sealed this

Eleventh Day of October, 2005

JON W. DUDAS
*Director of the United States Patent and Trademark Office*